(12) United States Patent
Lee et al.

(10) Patent No.: US 7,510,396 B2
(45) Date of Patent: Mar. 31, 2009

(54) DISPOSABLE DENTAL PROPHYLAXIS APPARATUS CAPABLE OF DISCHARGING PREDETERMINED AMOUNT OF DENTIFRICE MATERIAL THEREFROM

(76) Inventors: Kwang S. Lee, 11731 Welebir St., Loma Linda, CA (US) 92354; Duke K. Ghim, 10720 Lakewood Blvd., #335, Downey, CA (US) 90241

( * ) Notice: Subject to any disclaimer, the term of this patent is extended or adjusted under 35 U.S.C. 154(b) by 108 days.

(21) Appl. No.: 11/602,094

(22) Filed: Nov. 21, 2006

(65) Prior Publication Data

US 2008/0070188 A1 Mar. 20, 2008

(30) Foreign Application Priority Data

Sep. 15, 2006 (KR) ...................... 10-2006-0089786

(51) Int. Cl.
*A61C 5/04* (2006.01)
*A61C 1/12* (2006.01)
*A61C 3/03* (2006.01)
*A61C 3/06* (2006.01)

(52) U.S. Cl. .......................... 433/125; 433/89; 433/124; 433/133

(58) Field of Classification Search ................. 433/125, 433/89–90, 133, 124, 166; 222/386–390, 222/95, 105, 566–574; 15/22.1
See application file for complete search history.

(56) References Cited

U.S. PATENT DOCUMENTS

| 4,266,933 | A |  | 5/1981 | Warden et al. |
| 5,642,994 | A | * | 7/1997 | Chipian et al. ................. 433/82 |
| 5,642,995 | A | * | 7/1997 | Bailey ......................... 433/115 |
| 6,257,886 | B1 |  | 7/2001 | Warner |
| 7,029,278 | B2 | * | 4/2006 | Pond ........................... 433/125 |

* cited by examiner

*Primary Examiner*—Ralph A Lewis
*Assistant Examiner*—Yogesh Patel
(74) *Attorney, Agent, or Firm*—Louis F. Teran (57) ABSTRACT

The present invention relates to a hand tool used by dental professionals to polish a patient's tooth. The hand tool can be connected to a hand motor used to rotate a wheel cup with a plurality of grinding wings that rub against the patient's tooth as a predetermined amount of dentifrice material is discharged directly on the patient's tooth through a drain hole within the wheel cup. The dentifrice material is discharged from a tube that is assembled in the housing of the hand tool. The tube has a plurality of folds formed on the tube body in such a manner as to be folded by a given distance while being compressed to discharge the dentifrice material therefrom. The tube is compressed by a link with a push button that is guided in the forward direction as it is pushed by a finger.

10 Claims, 11 Drawing Sheets

DISPOSABLE DENTAL PROPHYLAXIS APPARATUS CAPABLE OF DISCHARGING PREDETERMINED AMOUNT OF DENTIFRICE MATERIAL THEREFROM

BACKGROUND OF THE INVENTION

1. Field of the Invention

The present invention relates to a disposable dental prophylaxis apparatus for use in scaling, grinding, or polishing the surface of teeth in dental fields, and more particularly, to a disposable dental prophylaxis apparatus that is capable of discharging a predetermined amount of dentifrice material therefrom such that dentists can effectively perform their desired dental operations with the dentifrice material discharged therefrom.

2. Description of the Prior Art

Presently, there have been provided various kinds of disposable dental prophylaxis devices in the art. For the full comprehension of this invention, two prior art inventions among them are suggested in this description, first of which is disclosed in U.S. Pat. No. 4,266,933 entitled 'ROTARY DENTAL POLISHING APPARATUS' and filed on May 12, 1981 (hereinafter, referred to as "first prior art"), and second of which is disclosed in U.S. Pat. No. 6,257,886 entitled 'DISPOSABLE DENTAL PROPHYLAXIS ANGLE' and filed on Jul. 10, 2001 (hereinafter, referred to as "second prior art").

Referring first to the first prior art, the rotary dental polishing apparatus includes a hand piece adapted for controlling rotating operations, a housing adapter, and a cartridge for housing polishing paste therein.

In the first prior art, the cartridge may be in a linear or perpendicular shape with respect to the hand piece, and it has a ribbon type of screw conveyor mounted at the inside thereof and a polishing cup coupled at one side end portion thereof.

The cartridge and the polishing cup have respective holes formed in the middle portions thereof in such a manner as to communicate with each other, such that the polishing paste at the inside of the cartridge can flow into the polishing cup.

On the other hand, while the housing adapter or a cylinder housing coupled to the hand piece is being rotated by means of the mechanism of gears connected thereto, at the state where the ribbon type of screw conveyor mounted at the inside of the cartridge stops without rotating, the polishing paste charged at the inside of the cartridge is supplied to the polishing cup through the hole formed in the middle portion thereof.

Unfortunately, the first prior art is well explained with the help of the drawings and description, but actually, it fails to satisfy some practical conditions such as the structural conditions in a manufacturing process, the cost conditions in a distributing process, and the physical operation principles in practical uses, such that the product is not really made or used at all in this related art up to now after this patent has been granted. The reason why the first prior art is not available can be apparently appreciated from the structural characteristics the presently popular disposable dental prophylaxis apparatus have had.

Referring now to the disposable dental prophylaxis apparatus presently popular in the art, the adapter that is adapted for being inserted into a hand motor has the whole length of about 46 mm. Next, referring to the thickness of the adapter, that is, to the diameter of the tube, the thick portion has a diameter of about 11 mm and the thin portion has a diameter of about 8.4 mm, such that it is appreciated from the sizes of the adapter that it is a very tiny part. More particularly, the head portion of the adapter that is inserted deeply up to the back tooth of a patient's mouth has a diameter of about 8.4 mm and a height of about 10.5 mm.

Specifically, if the thickness of the adapter tube of about 2 mm is subtracted from the whole diameter thereof, the inner diameter of the head portion is just 6.4 mm. By the way, according to the first prior art, the ribbon type of conveyor is housed in the tiny space of the cartridge and further, the polishing paste is charged at the inside of the cartridge, which fails to sufficiently consider the supply and demand laws that should be satisfied from the manufacturing process to the practical use process.

In addition to the structural difficulties the first prior art has as mentioned above, it has the operational difficulties wherein the screw conveyor stops while the cartridge is being rotated, thereby discharging the polishing paste therefrom. Physically, this is like the principle where an automobile starts at the state of being braked, and in this case, as a substantially strong force is applied to the inside of the cartridge, the conveyor becomes twisted, which makes it impossible to discharge the polishing paste therefrom. Furthermore, the rotating force is not transferred well by the application of the substantially strong force, which causes power braking such that the gears adapted to be in engagement with each other are abrasive to run idle.

For these reasons, it is found that the patent right of the first prior art is terminated, while not put into practical use.

Referring next to the second prior art, it can be appreciated that the second prior art is a much more improved invention than the first prior art.

Apparently, the second prior art is more excellent than the first prior art. The first prior art employs the rotary cartridge having the ribbon type conveyor mounted therein, and contrarily, the second prior art employs a structure wherein a dentifrice material is charged into a housing and is then discharged by the pushing force of a piston.

According to a first aspect of the second prior art, if an actuator surrounding a drive shaft is pushed to move a flange forwardly, a dentifrice material that is charged in a housing flows to an upper channel portion and is supplied to a prophylaxis cup through a delivery channel portion. According to a second aspect of the second prior art, if a cam is pressed to forwardly move a push rod having an inclined face formed at one side end in such a manner as to surround the drive shaft, a spring is compressed to make a dam push the actuator such that the dentifrice material is discharged to the prophylaxis cup through the upper channel portion. According to a third aspect of the second prior art, a plate-like primary drive gear is mounted at the end portion of the drive shaft, having a through hole adapted for discharging the dentifrice material therefrom, such that the dentifrice material can be supplied to the prophylaxis cup.

However, according to the above-mentioned aspects of the second prior art, as the charged dentifrice material undesirably sticks to the shaft when the shaft is rotated, power braking severely occurs on a hand piece motor, which results in high heat generation on the hand piece motor.

In addition, as the shaft is rotated at the state of being buried into the dentifrice material, the rotating force of the shaft is not exerted well as if a boat is not advanced well by the application of high water pressure caused by the rotation of a screw under the water.

Thus, the prophylaxis cup that has to be rotated at a high speed is not really rotated rapidly, which loses its friction function against a patient's tooth. As the shaft and the dentifrice material rubbing against each other generate large heat at the inside of the shaft, the dentifrice material may be changed in its original quality.

Moreover, the second prior art is very complicated in its structure, which makes it hard to perform a mold-manufacturing process and an injection molding process, and specifically, even though all parts are made, they could not be assembled structurally with one another, such that no final product is made up to present.

SUMMARY OF THE INVENTION

Accordingly, the present invention has been made in view of the above-mentioned problems occurring in the prior art, and it is an object of the present invention to provide a disposable dental prophylaxis apparatus capable of discharging a predetermined amount of dentifrice material therefrom that is configured to have an adequate structure to the sizes of general disposable dental prophylaxis devices widely used in the art, thereby enabling the product to be made in great quantities and at inexpensive costs and providing many conveniences to both of dentists and patients.

It is another object of the present invention to provide a disposable dental prophylaxis apparatus capable of discharging a predetermined amount of dentifrice material therefrom that is compatible to existing hand motors, without changing any new one, such that when dentists who use conventional disposable dental prophylaxis devices employ the disposable dental prophylaxis apparatus of the present invention, they can utilize it skillfully, without feeling any inconvenience while in use.

To accomplish the above objects, according to the present invention, there is provided a disposable dental prophylaxis apparatus capable of discharging a predetermined amount of dentifrice material therefrom including: a housing adapted for assembling all parts therein; a wheel gear having an upper end portion disposed perpendicularly in engagement with a joint gear and having a lower end portion rotatably coupled with a wheel cup; the wheel cup made of a soft rubber material and coupled to the lower end portion of the wheel gear in such a manner as to rub against a tooth for grinding or polishing the tooth; the joint gear adapted to be inserted in a lengthwise direction of the housing in such a manner as to be in engagement with the wheel gear at one end portion thereof and coupled to a hand motor at the other end portion thereof for receiving a rotating force from the hand motor; a tube having relatively thick front and back plates, a relatively thin body having a plurality of folds formed thereon in such a manner as to be narrow at the inside thereof and large at the outside thereof, and a neck portion formed in the middle portion of one side thereof, the neck portion having a fixing ring formed along the peripheral surface of a tube inlet and a compressing ring spaced apart from the fixing ring; a link having ratchets elastically formed on both sides of the rear end portion on a link shaft having a push panel formed at the front side thereof and a push button formed extendedly from a pillar protruded upwardly from the middle portion of the rear end portion thereof, the push button having an inclination angle of about 70°; and a lid having a link guide openably cut in one direction thereof, corner grooves formed at the both side corners thereof by means of groove gouging, and a lid rim formed along the edges of a lid plate.

The housing has a head portion inclined upwardly at the front side thereof and a back portion extended from the head portion, the back portion having a tube room formed for housing the dentifrice material-charging tube therein and a link room formed for pressing the tube to discharge the dentifrice material from the tube. At this time, the housing has the whole length of about 65 mm, a height of about 16 mm, and a width of about 13 mm.

On the other hand, there is provided a partition between the tube room and the link room, for defining the tube room and the link room in the housing and at the same time for guiding the link. At this time, the link room is opened at the rear portion thereof and is provided with pillar-like locking protrusions that are formed at the both sides of the opened rear portion thereof for stopping the movement of the lid and with a plurality of teeth formed at given intervals along the both vertical wall sides thereof. At the time, each of the teeth has a module of about 1.5 mm, while being oblique at one plane thereof and being perpendicular at the other plane thereof.

Also, the tube room has a curved drain hole formed along the inside middle portion of the head portion of the housing, for discharging the dentifrice material therealong. At this time, the drain hole has a diameter of about 1.5 mm.

The wheel gear has a force stabilizing ring formed along the upper end periphery thereof for preventing the generation of shaking during rotation and a drain hole formed along the inside middle portion thereof for discharging the dentifrice material therefrom, the drain hole having a diameter of about 1.5 mm.

The wheel cup has a drain hole formed for moving the dentifrice material flowing from the drain hole of the wheel gear to a friction space portion and a plurality of grinding wings, each of the grinding wings having the lower face larger than the upper face thereof.

The joint gear has a vibration-absorbing groove adapted for absorbing the vibration generated from the extended portion thereof, a reinforcing shaft for preventing the generation of twisting thereon, and a plurality of force stabilizing rings for maintaining the concentric force generated while being rotated at a high speed.

The tube has the relatively thick front and back plates, the relatively thin body having the plurality of folds formed thereon in such a manner as to be narrow at the inside thereof and large at the outside thereof, and the neck portion formed in the middle portion of one side thereof, the neck portion having the fixing ring formed along the peripheral surface of the tube inlet and the compressing ring spaced apart from the fixing ring.

The link has the push panel formed at the front side thereof in such a manner as to abut against the back face of the tube for pushing the tube, the ratchets elastically formed on both sides of the rear end portion thereof, the push button extended from the pillar protruded upwardly from the middle portion of the rear end portion thereof, the push button having an inclination angle of about 70°, such that if the push button is pushed, the dentifrice material in the tube is discharged from the tube.

The lid is finally assembled with the housing, for preventing the link guide adapted for movement of the link from being deviated from the link.

The invention may be described with greater clarity and particularity by reference to the accompanying drawings.

DESCRIPTION OF THE DRAWINGS

The above and other objects, features and advantages of the present invention will be apparent from the following detailed description of the preferred embodiments of the invention in conjunction with the accompanying drawings, in which:

FIG. 2b is an enlarged sectional view showing the parts in a circle 'A' of FIG. 2a;

FIG. 3b is an enlarged sectional view showing the parts in a circle 'A' of FIG. 3a;

FIG. 12 is a sectional view taken along the line B-B' of FIG. 2a;

FIG. 13 is a sectional view taken along the line C-C' of FIG. 2a;

FIG. 17b is an enlarged sectional view showing the parts in a circle 'A' of FIG. 17a;

FIG. 18b is one side view of the stop key of FIG. 18a;

DESCRIPTION OF THE EMBODIMENT

Hereinafter, an explanation of a disposable dental prophylaxis apparatus capable of discharging a predetermined amount of dentifrice material therefrom according to the present invention will be given with reference to the attached drawings.

Figure 1:
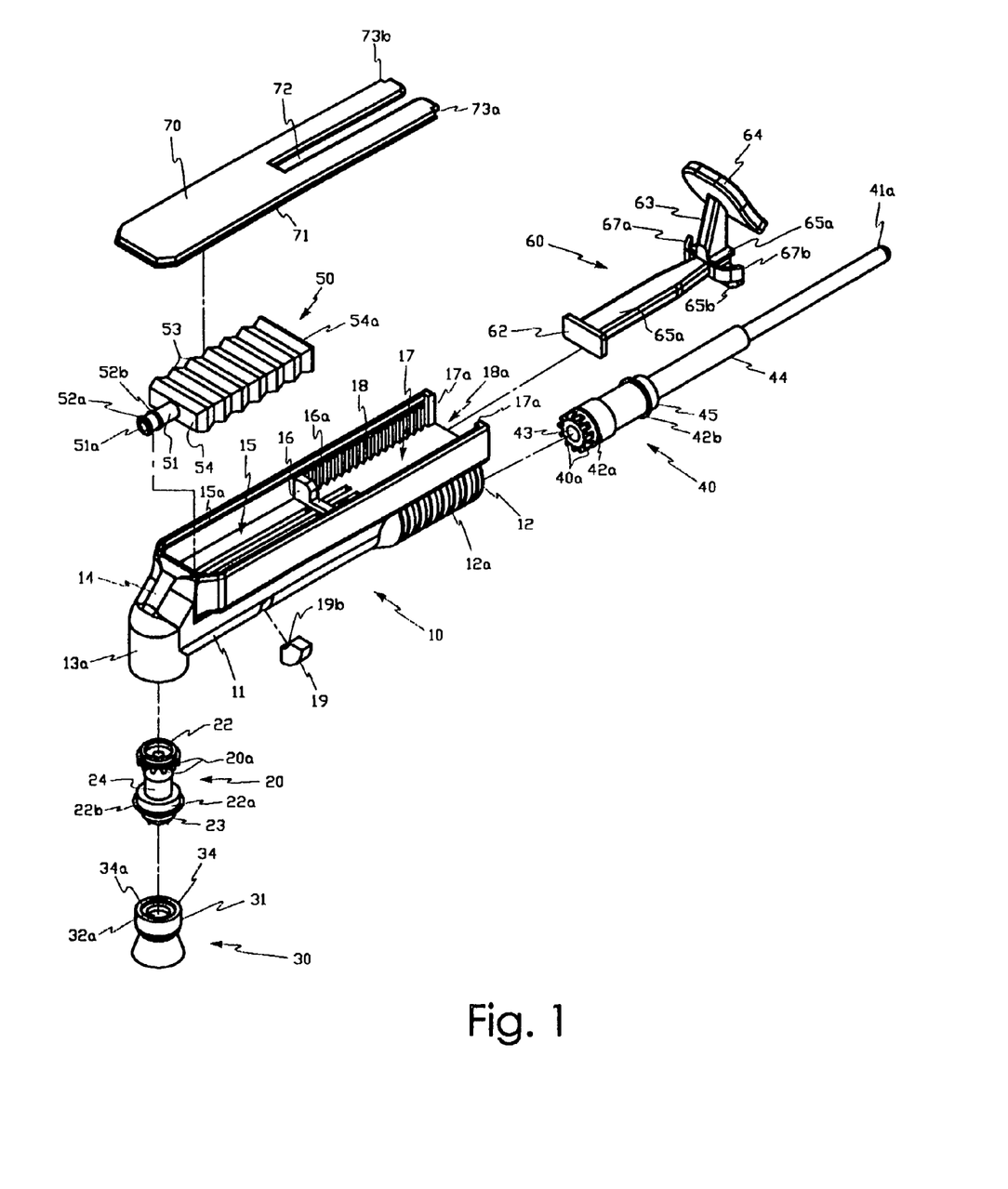
FIG. 1 is an exploded perspective view showing a disposable dental prophylaxis apparatus capable of discharging a predetermined amount of dentifrice material therefrom according to the present invention.
Figure 2A:
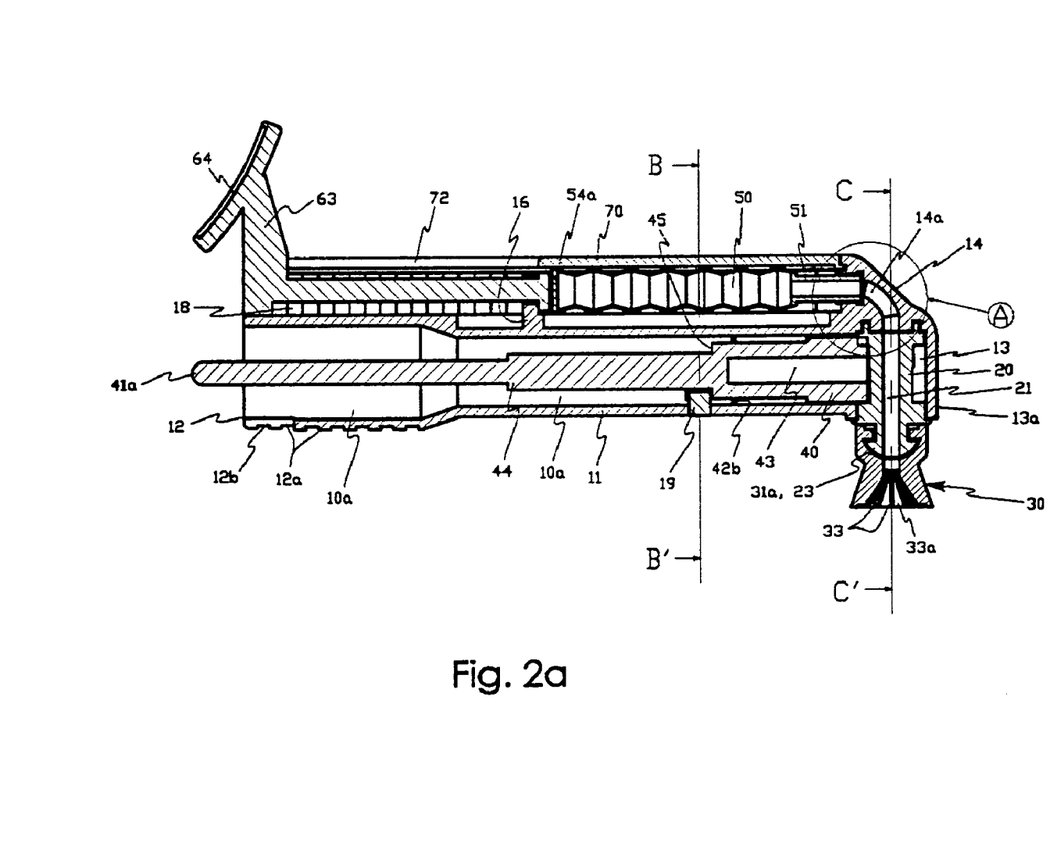
FIG. 2a is a sectional view taken along the line of A-A' of FIG. 10.
Figure 2B:
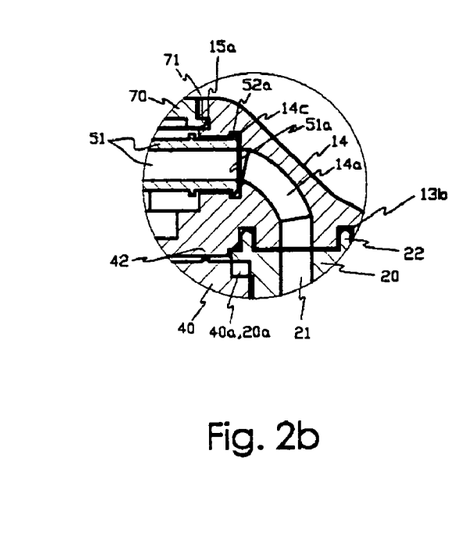
Figure 3A:
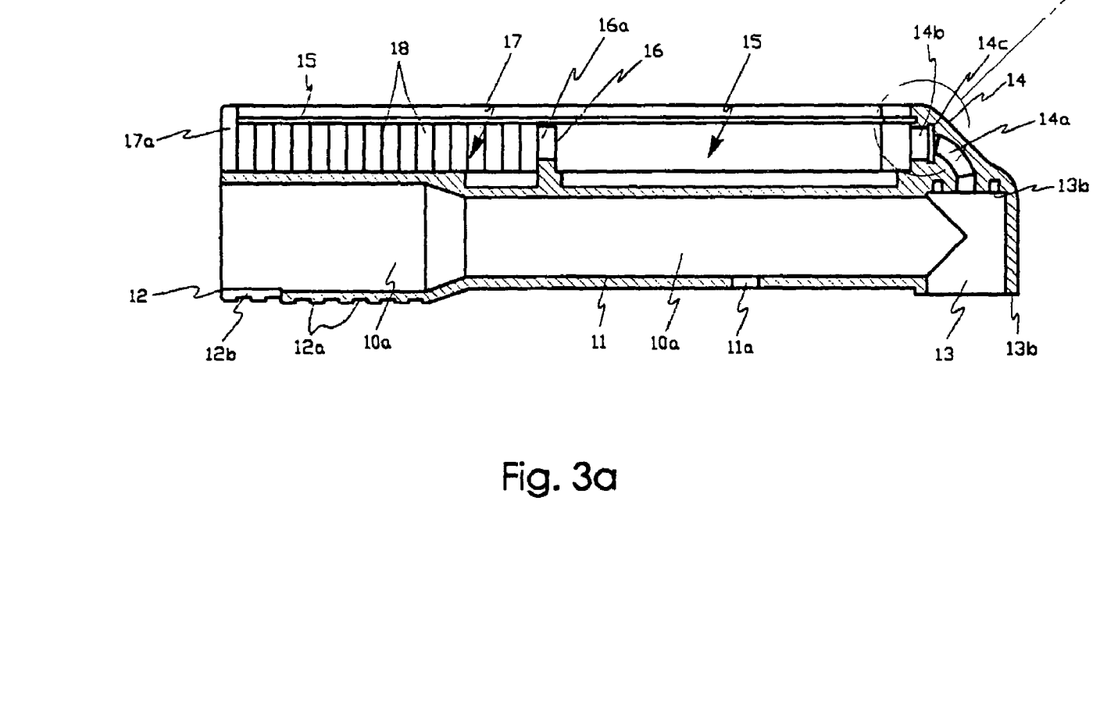
FIG. 3a is a sectional view showing a configuration of a housing of the disposable dental prophylaxis apparatus of the present invention.
Figure 3B:
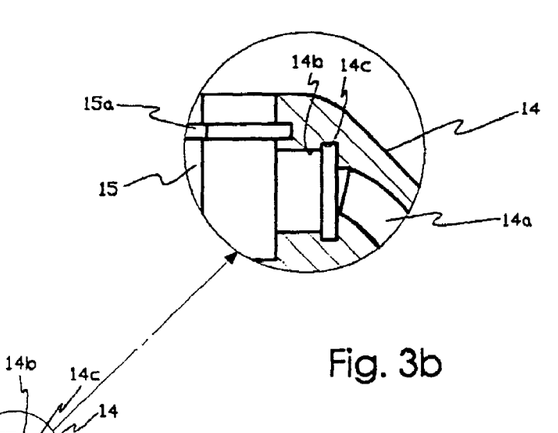
Figure 4:
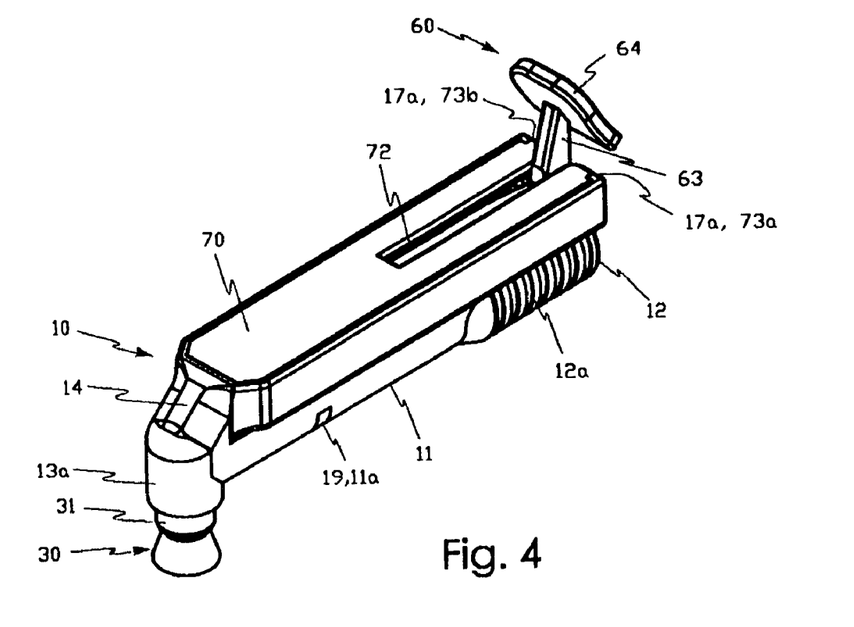
FIG. 4 is a perspective view showing the assembled state of the disposable dental prophylaxis apparatus of the present invention.
Figure 5:
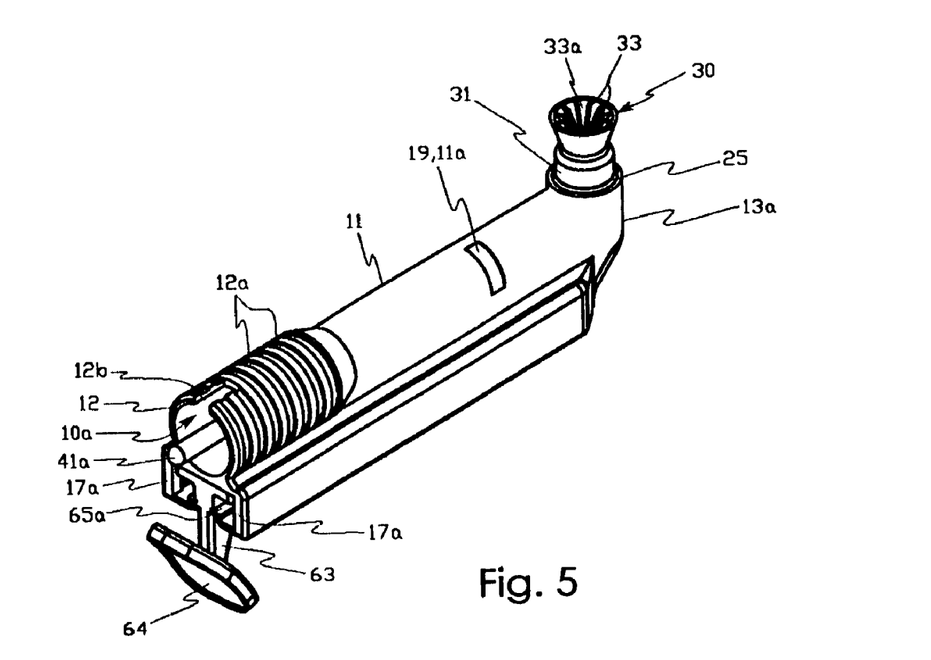
FIG. 5 is a bottom perspective view of FIG. 4.
Figure 6:
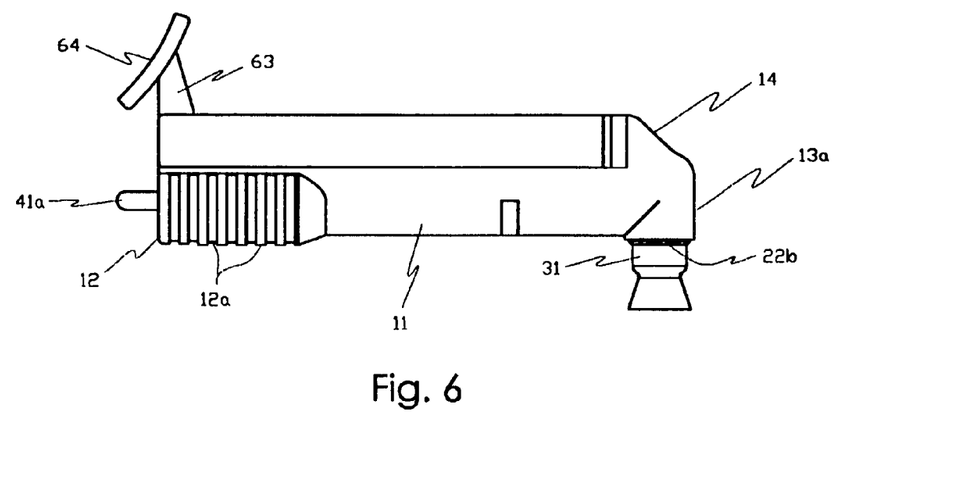
FIG. 6 is a front view of the disposable dental prophylaxis apparatus of the present invention.
Figure 7:
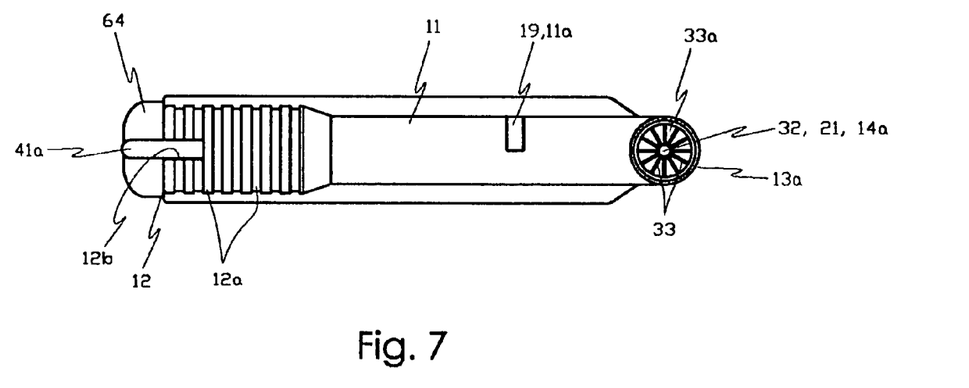
FIG. 7 is a bottom view of the disposable dental prophylaxis apparatus of the present invention.
Figure 8:
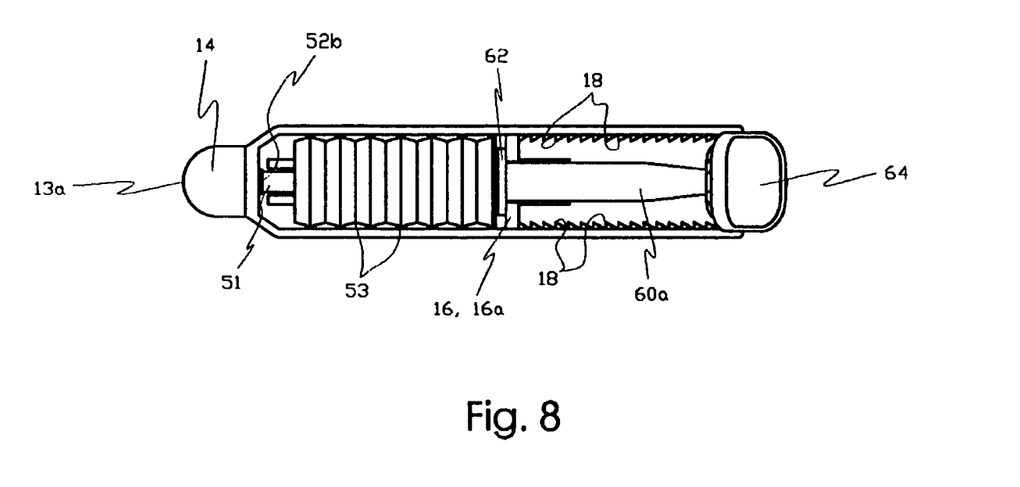
FIG. 8 is a plan view showing a state where a lid is removed in the disposable dental prophylaxis apparatus of the present invention.
Figure 9:
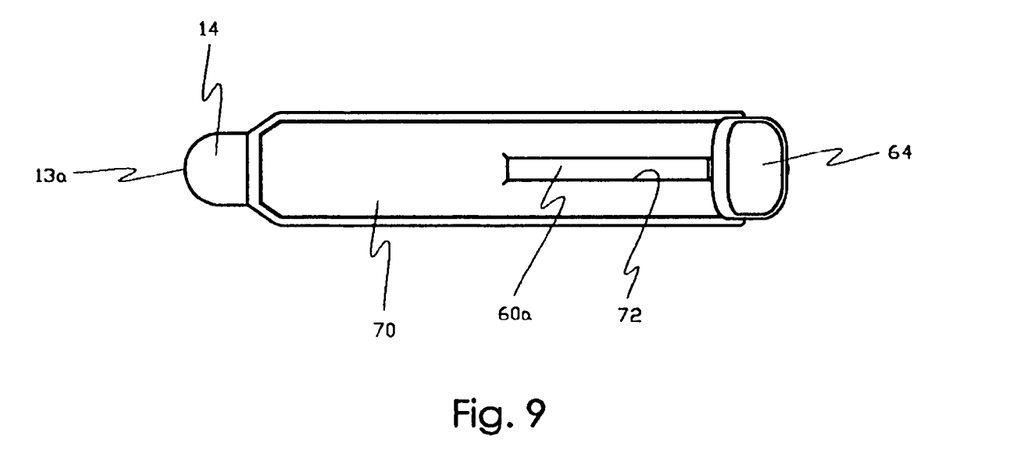
FIG. 9 is a plan view showing the assembled state of the disposable dental prophylaxis apparatus of the present invention.
Figure 10:
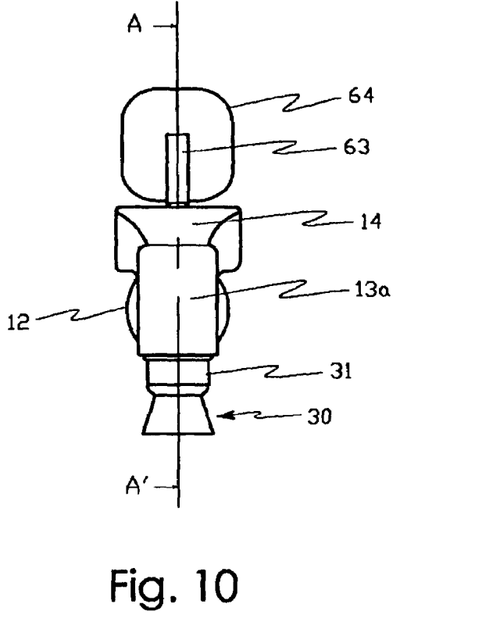
FIG. 10 is a left side view of the disposable dental prophylaxis apparatus of the present invention.
Figure 11:
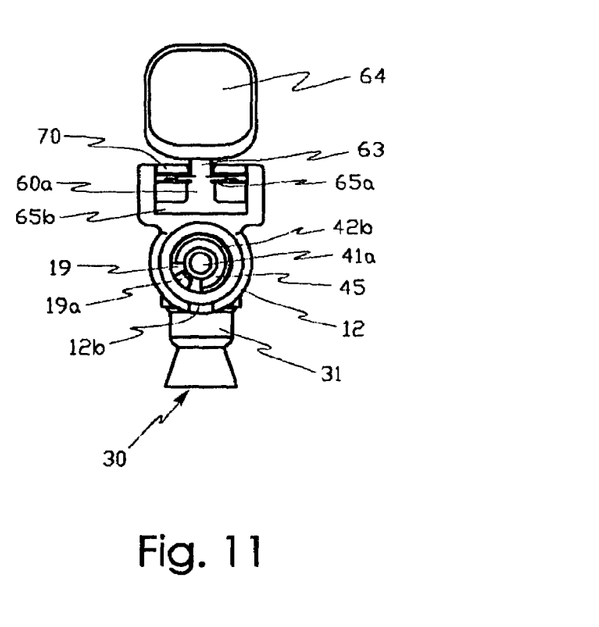
FIG. 11 is a right side view of the disposable dental prophylaxis apparatus of the present invention.
Figure 12:
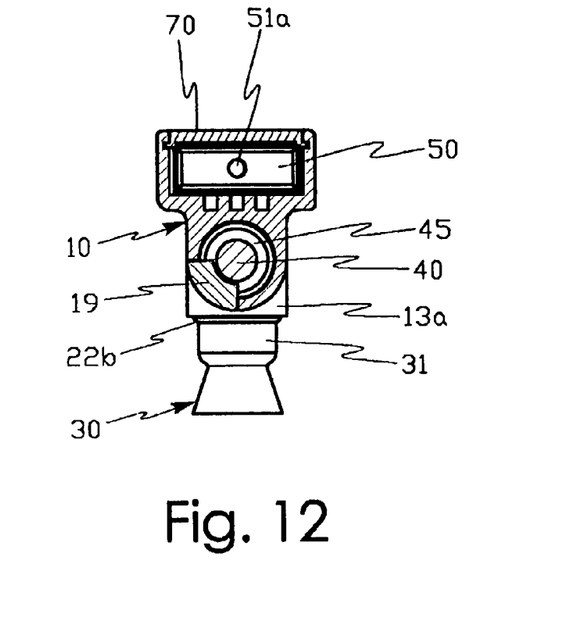
Figure 13:
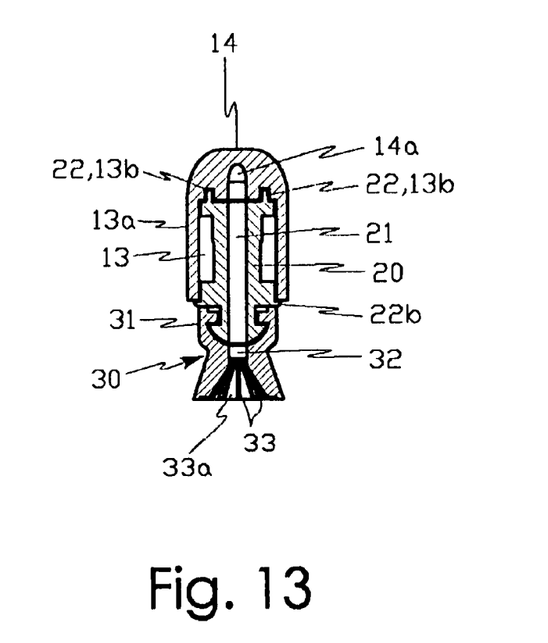
Figure 14:
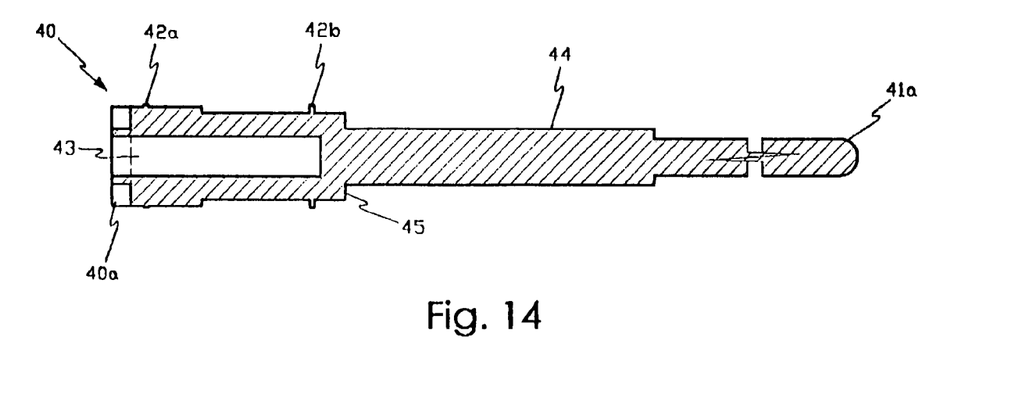
FIG. 14 is a sectional view showing a joint gear of the disposable dental prophylaxis apparatus of the present invention.
Figure 15:
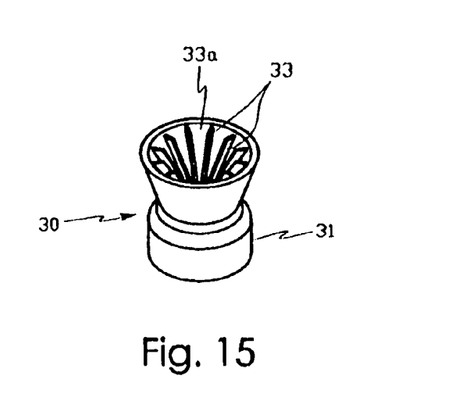
FIG. 15 is a perspective view showing the bottom portion of a wheel cup of the disposable dental prophylaxis apparatus of the present invention.
Figure 16:
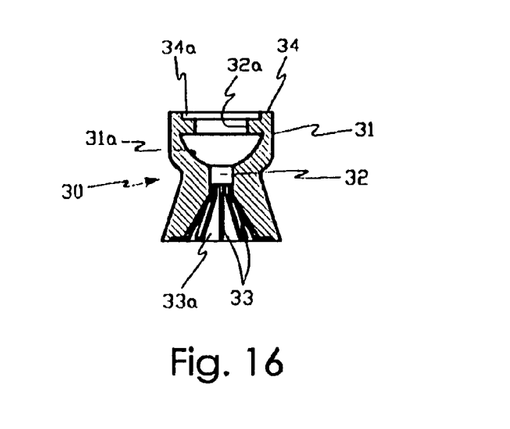
FIG. 16 is a sectional view showing the wheel cap of the disposable dental prophylaxis apparatus of the present invention.
Figure 17A:
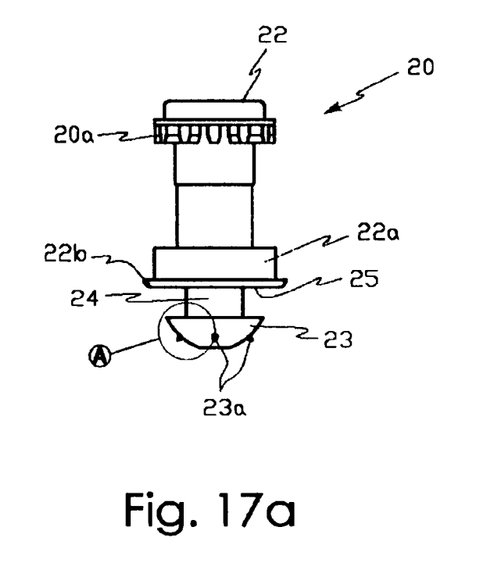
FIG. 17a is a front view showing the wheel cap of the disposable dental prophylaxis apparatus of the present invention.
Figure 17B:
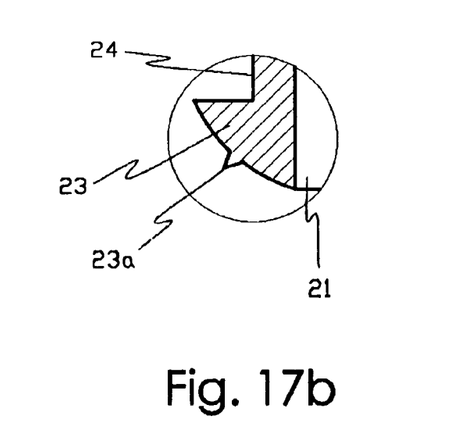
Figure 18A:
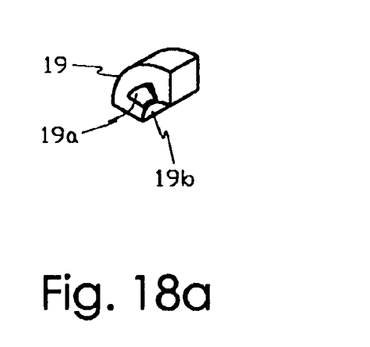
FIG. 18a is a perspective view showing a stop key of the disposable dental prophylaxis apparatus of the present invention.
Figure 18B:
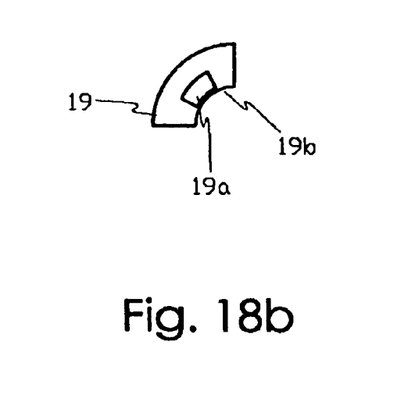
Figure 19:
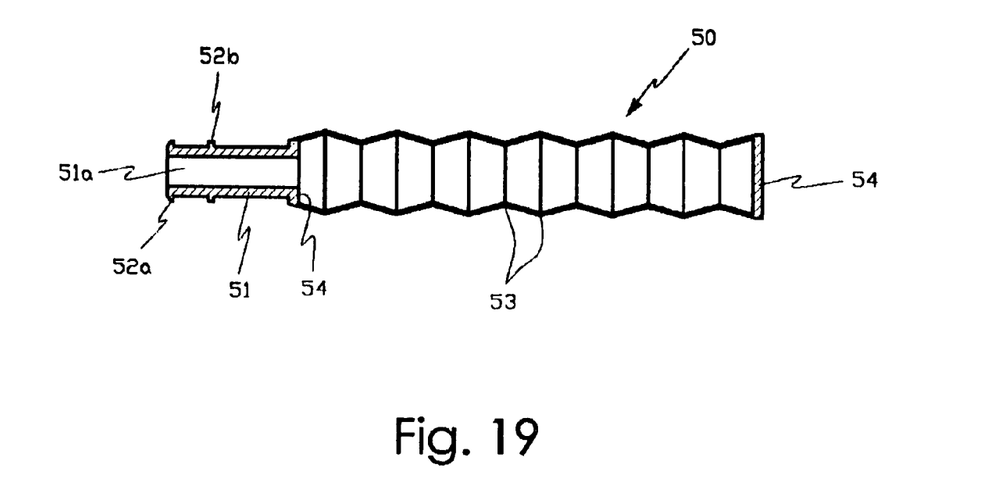
FIG. 19 is a sectional view showing a dentifrice material-charging tube of the disposable dental prophylaxis apparatus of the present invention.
Figure 20:
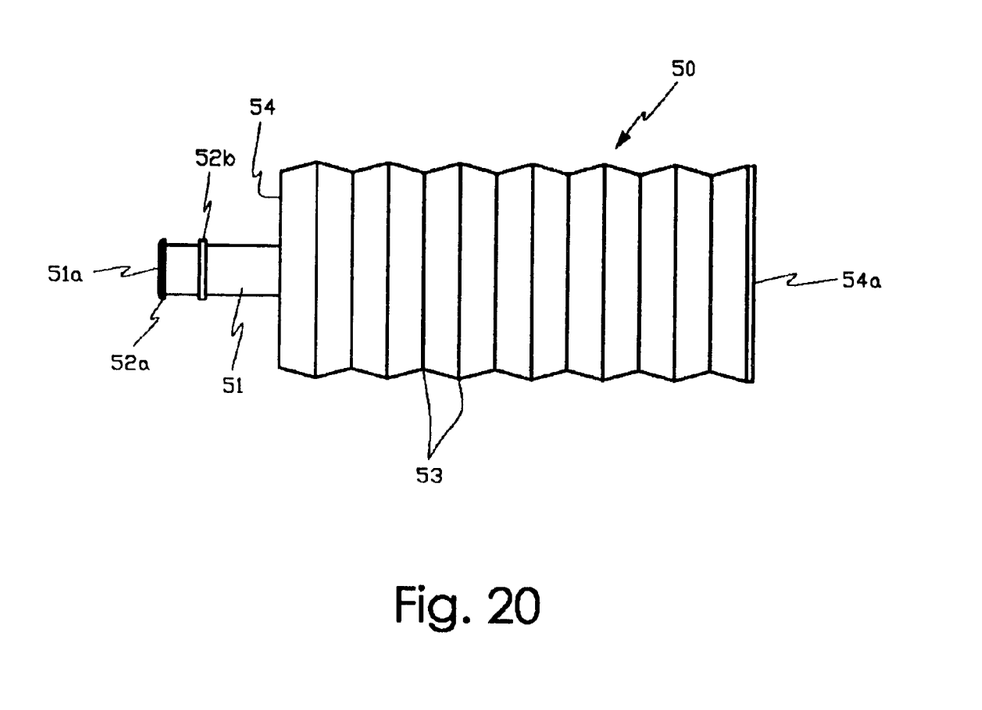
FIG. 20 is a plan view showing the dentifrice material-charging tube of the disposable dental prophylaxis apparatus of the present invention.

FIG. 1 is an exploded perspective view showing a disposable dental prophylaxis apparatus capable of discharging a predetermined amount of dentifrice material therefrom according to the present invention, FIG. 2a is a sectional view taken along the line of A-A' of FIG. 10, FIG. 2b is an enlarged sectional view showing the parts in a circle 'A' of FIG. 2a, FIG. 3a is a sectional view showing a configuration of a housing of the disposable dental prophylaxis apparatus of the present invention, FIG. 3b is an enlarged sectional view showing the parts in a circle 'A' of FIG. 3a, FIG. 4 is a perspective view showing the assembled state of the disposable dental prophylaxis apparatus of the present invention, FIG. 5 is a bottom perspective view of FIG. 4, FIG. 6 is a front view of the disposable dental prophylaxis apparatus of the present invention, FIG. 7 is a bottom view of the disposable dental prophylaxis apparatus of the present invention, FIG. 8 is a plan view showing a state where a lid is removed in the disposable dental prophylaxis apparatus of the present invention, FIG. 9 is a plan view showing the assembled state of the disposable dental prophylaxis apparatus of the present invention, FIG. 10 is a left side view of the disposable dental prophylaxis apparatus of the present invention, FIG. 11 is a right side view of the disposable dental prophylaxis apparatus of the present invention, FIG. 12 is a sectional view taken along the line B-B' of FIG. 2a, FIG. 13 is a sectional view taken along the line C-C' of FIG. 2a, FIG. 14 is a sectional view showing a joint gear of the disposable dental prophylaxis apparatus of the present invention, FIG. 15 is a perspective view showing the bottom portion of a wheel cap of the disposable dental prophylaxis apparatus of the present invention, FIG. 16 is a sectional view showing the wheel cap of the disposable dental prophylaxis apparatus of the present invention, FIG. 17a is a front view showing the wheel cap of the disposable dental prophylaxis apparatus of the present invention, FIG. 17b is an enlarged sectional view showing the parts in a circle 'A' of FIG. 17a, FIG. 18a is a perspective view showing a stop key of the disposable dental prophylaxis apparatus of the present invention, FIG. 18b is one side view of the stop key of FIG. 18a, FIG. 19 is a sectional view showing a dentifrice material-charging tube of the disposable dental prophylaxis apparatus of the present invention, and FIG. 20 is a plan view showing the dentifrice material-charging tube of the disposable dental prophylaxis apparatus of the present invention.

According to the present invention, there is provided a disposable dental prophylaxis apparatus capable of discharging a predetermined amount of dentifrice material therefrom includes a housing 10 serving as a body, a wheel gear 20, a wheel cup 30, a joint gear 40, a tube 50, a link 60, and a lid 70.

In more detail, the disposable dental prophylaxis apparatus according to the present invention includes: a housing 10 having a drain hole 14a adapted for discharging a dentifrice material therefrom, a tube room 15 adapted for mounting a dentifrice material-charging tube 50 therein, and a link room 17 having a plurality of teeth 18 formed along the both inner wall surfaces for adjustably discharging the dentifrice material in predetermined amounts from the tube 50; a wheel gear 20 having a drain hole 21 adapted for inducing the dentifrice material flowing from the drain hole 14a of the housing 10 to a wheel cup 30 adapted for rubbing against a patient's tooth; the wheel cup 30 having a drain hole 32 formed for receiving the dentifrice material induced from the drain hole 21 of the wheel gear 20; the tube 50 adapted to be charged with the dentifrice material and having a plurality of folds 53 adapted to be compressed gradually as the dentifrice material is discharged therefrom in the predetermined amounts; and a link 60 adapted for compressing the tube 50 such that the dentifrice material is discharged from the tube 50.

As shown in FIGS. 3a and 3b, the housing 10 serving as a body of the disposable dental prophylaxis apparatus of the present invention has a thick tube 12 and a thin tube 11 formed stepped on the lower portion thereof, the thick tube 12 having a concave-convex portion 12a formed along the outer periphery thereof for preventing the sliding movement thereof and the thin tube 11 having a head portion 13a formed perpendicularly on the end portion thereof.

At this time, the thick tube 12 and the thin tube 11 serve as a hollow portion 10a formed along the inside thereof in such a manner as to be coupled with the joint gear 40 for driving the joint gear 40 therein, the hollow portion 10a being of a generally circular or square sectional shape. The head portion 13a is provided with a wheel room 13 having a force stabilizing groove 13b formed having a substantially circular shape on a ceiling portion thereof in such a manner as to be coupled with the wheel gear 20 as will be discussed below.

Further, the housing 10 has a tube room 15 and a link room 17 disposed on the top portions of the thick tube 12 and the thin tube 11, for housing the tube 50 and the link 60 therein.

At this time, the link room 17 has an entrance 18a formed opened at the back side thereof, pillar-like locking protrusions 17a formed at the both sides of the entrance 18a, and a plurality of teeth 18 formed at given intervals along the both inner wall surfaces thereof.

The tube room 15 has an oblique head portion 14 formed at one end thereof, the head portion 14 having a curved drain hole 14a formed along the middle portion thereof. The drain hole 14a is a passageway for movement of the dentifrice material discharged from the tube 50. The head portion 14 further has a neck portion insertion hole 14b formed at the inlet thereof for tightly fitting the tube 50 thereto and a ring groove 14c formed along the inner periphery of the neck portion insertion hole 14b for insertedly fixing a fixing ring 52a of a tube inlet 51a of the tube 50 therealong.

On the other hand, the housing 10 further has a partition 16 disposed between the tube room 15 and the link room 17, the partition 16 having a partition groove 16a formed in the middle portion thereof. The partition groove 16a and the partition 16 serve to guide the movement of the link 60.

Furthermore, the housing 10 has an insertion groove 15a formed at a given depth along the top wall sides of the tube room 15 and the link room 17 in such a manner as to be coupled with the lid 70 therealong.

On the other hand, each of the plurality of teeth 18 desirably has a module in a range between 1 mm and 1.5 mm, and the drain hole 14a desirably has a diameter of about 1.5 mm.

As shown in FIGS. 17a and 17b, next, the wheel gear 20 that is adapted to be coupled to the wheel room 13 of the housing 10 has an upwardly protruded horizontal force stabilizing ring 22 formed along the circumferential direction of the upper portion thereof and a plurality of gear forming members 20a formed radially at given intervals just below the horizontal force stabilizing ring 22.

The wheel gear 20 is provided with a body part having a vertical force stabilizing ring 22a formed stepped vertically on the outer periphery thereof in such a manner as to rub against the inner periphery of the wheel room 13, a wing ring 22b formed along the lower end portion thereof, the wing ring 22b having a relatively large peripheral surface, and a bottom face 25 adapted for tightly abutting against a close contact face 34 of the wheel cup 30.

The wheel gear 20 further has a relatively thin neck portion 14 formed on the lower portion of the bottom face 25 in such a manner as to be surrounded with a coupling hole 32a of the wheel cup 30 and has a generally hemispherical head portion 23 formed at the lowermost end portion thereof, the head portion 23 having a plurality of idle preventing needles 23a formed on the peripheral surface thereof.

At this time, each of the plurality of idle preventing needles 23a desirably has a protruded length of about 0.3 mm.

The wheel cup 30 that tightly abuts against the head portion 23, the neck portion 24, and the bottom face 25 has, as shown in FIG. 16, a close contact face 34 and a close contact groove 34a formed along the top portion thereof for enhancing the close contacting force thereof with the wheel gear 20 when coupled with the bottom face 25 of the wheel gear 20, and has the coupling hole 32a and a head-coupling member 31a formed in the inside middle portion thereof for inserting the neck portion 24 and the head portion 23 of the wheel gear 20 thereinto.

Further, the wheel cup 30 has a drain hole 32 formed to pass through the upper and down portions along the inside middle portion thereof for discharging the dentifrice material therethrough, a friction space portion 33a formed at the lower portion extended from the drain hole 32 for allowing the dentifrice material supplied from the drain hole 32 to rub against a patient's tooth, and a plurality of grinding wings 33 formed at the lower portion thereof for brushing the patient's tooth, each of the plurality of grinding wings 33 having a relatively larger lower face than the upper face thereof.

As shown in FIGS. 1 and 14, the joint gear 40 has a vibration-absorbing groove 43 formed in the middle portion of one side thereof for absorbing the vibration of the gear shaft generated while rotated and has a plurality of gear forming members 40a formed at the front end portion thereof in such a manner as to be in engagement with the gear forming members 20a of the wheel gear 20.

The joint gear 40 further has a key locking protrusion 45 and a reinforcing shaft 44 formed stepped perpendicularly along the middle portion of the gear body, the reinforcing shaft 44 being adapted for increasing the strength of the gear shaft, and has two force stabilizing rings 42a and 42b formed spaced apart from each other along the outer peripheral surface thereof.

As shown in FIGS. 19 and 20, the tube 50 has a fixing ring 52a formed along the peripheral surface of the tube inlet 51a discharging the dentifrice material therefrom, the fixing ring 52a being adapted to be inserted into the neck insertion hole 14b of the housing 10 for preventing the separation from the tube 50 and also adapted to be tightly fitted to the ring groove 14c for preventing the discharged dentifrice material from being leaked from the tube 15.

Further, the tube 50 has a neck portion 51 having a compressing ring 52b formed along the outer periphery thereof such that as the tube 50 is pushed and inserted by holding the compressing ring 52b by means of tweezers, the tube 50 is mounted into the tube room 15.

Also, the tube 50 has relatively thicker front and back plates 54 and 54a than the tube body, for supporting the force applied when compressed by means of the link 60, and has a plurality of folds 53 formed on the tube body in such a manner as to be folded by a given distance while being compressed to discharge the dentifrice material therefrom.

As shown in FIGS. 1 and 2a, next, the link 60 has a push panel 62 formed at the front end side thereof for compressing the back plate 54a of the tube 50 in a close contact relation with the back plate 54a, and has ratchets 67a and 67b elastically formed on both sides of the rear end portion thereof in such a manner as to move forwardly in one direction along the teeth 18 of the link room 17 and contrarily to prevent the backward movement thereof.

Each of the ratchets 67a and 67b has guides 65a and 65b formed on the upper and lower portions of the rear side thereof for guiding the sliding movement of the link 60, and has a vertical pillar 63 formed extendedly on the top portion thereof, the pillar 63 having a push button 64 inclined at a given angle such that the push button 64 can be easily pressed by a finger.

Finally, as shown in FIG. 1, the lid 70 has a link guide 72 openably cut in one direction thereof for guiding the movement of the link 60, corner grooves 73a and 73b formed at the both side corners of the opened one side of the link room 17, and a lid rim 71 formed along the edges of a lid plate.

Now, an explanation of the use state of the disposable dental prophylaxis apparatus capable of discharging a predetermined amount of dentifrice material therefrom will be given hereinafter.

According to the present invention, the disposable dental prophylaxis apparatus capable of discharging a predetermined amount of dentifrice material therefrom has the tube 50 first charged with gel type of dentifrice material having a relatively low viscosity and then closes the tube 50 by means of the tube inlet 51a.

Next, the wheel cup 30 that is made of a soft rubber material is coupled with the head portion 23 of the wheel gear 20, and the head portion 23 should be completely inserted into the hollow portion of the wheel room 13.

On the other hand, referring to a method for coupling the wheel cup 30 with the head portion 23 of the wheel gear 20, first, as the head-coupling member 31a of a hemisphere shape that is formed large in the inside middle portion of thereof is extended, the head portion 23 is pushed toward the extended head-coupling portion 31a. Then, the round coupling cup 31 of the wheel cup 30 is turned to push inwardly along the peripheral surface thereof, such that the head portion 23 is conveniently mounted into the head-coupling portion 31a and at the same time the idle preventing needles 23a are penetrated onto the bottom face of the hemisphere portion of the head-coupling portion 31a, which enables the wheel cup 30 to be rotated together with the wheel gear 20 during the rotation of the wheel gear 20, without having any idle.

In more detail, when the wheel cup 30 is coupled with the head portion 23 of the wheel gear 20, the coupling hole 32a formed in the middle portion of the wheel cup 30 is opened to push the head portion 23 thereinto, and at this time, even though the outer peripheral surface of the coupling cup 31 is not necessarily pressed by a finger, the wheel cup 30 is contracted by the rubber characteristics thereof such that the inner peripheral surface of the coupling hole 32a comes in close contact with the neck portion 24. At the same time, at the state where the head portion 23 is inserted into the head-coupling member 31a of the wheel cup 30, it is tightly fitted thereto by the contraction of the wheel cup 30 such that the ends of the idle preventing needles 23a are penetrated into the inner surface of the head-coupling member 31a. At this time, as the close contact face 34 of the wheel cup 30 comes in close contact with the bottom face 25 of the wheel gear 20, the wheel cup 30 can be rotated together with the wheel gear 20 during the rotation of the wheel gear 20.

Then, after the wheel gear 20 has been coupled with wheel cup 30 as mentioned above, the gear-forming members 20a disposed on the head portion of the wheel gear 20 are inserted into the wheel room 13 defined in the housing 10.

As a result, the horizontal force stabilizing ring 22 mounted along the upper peripheral surface of the wheel gear 20 is fitted along the force stabilizing groove 13b of a round circle shape formed on the ceiling of the wheel room 13.

Additionally, the vertical force stabilizing ring 22a comes in almost close contact along the lower inner periphery of the wheel room 13, and the top surface of the wing ring 22b comes in almost close contact along the bottom periphery of the wheel room 13. At this state, the coupling of the wheel gear 20 with the joint gear 40 is conducted.

The gear-forming members 40a of the front portion of the joint gear 40 are first inserted into the thick tube 12 at the back side of the housing 10.

At this time, the outer peripheral surfaces of the force stabilizing rings 42a and 42b are inserted into the hollow portion 10a of the housing 10 in almost close contact relation with the hollow portion 10a, and on the other hand, the gear-forming members 40a are deeply inserted to be in engagement with the gear-forming members 20a of the wheel gear 20 coupled first with the wheel room 13.

On the other hand, even when the gear-forming members 40a of the joint gear 40 that are inserted into the hollow portion 10a of the housing 10 are not in engagement with the gear-forming members 20a of the wheel gear 20, one of the wheel gear 20 and the joint gear 40 is somewhat rotated in left and right directions such that the gear-forming members 20a and 40a are in engagement with each other.

After the joint gear 40 has been coupled with the wheel gear 20, then, a stop key 19 is forcedly fitted to the rectangular key hole 11a formed along the round peripheral surface of the thin tube 11 of the housing 10.

As the stop key 19 is fitted to the key hole 11a, a protrusion 19a is locked into the inner surface of the thin tube 11 such that the stop key 19 is not deviated from the thin tube 11, and the stop key 19 stops the locking protrusion 45 of the joint gear 40 at one side thereof for supporting the locking protrusion 45 and at the same time has an inwardly curved face 19b coupled with the reinforcing shaft 44 of the joint gear 40 near the reinforcing shaft 44 in such a manner as to be spaced from the reinforcing shaft 44 by a given distance. So, since the wheel gear 20 is in engagement with the joint gear 40, they are not separated from each other by the application of an external force, and also, since the locking protrusion 45 of the joint gear 40 is locked into the stop key 19, they are not separated from each other, such that the wheel gear 20 and the joint gear 40 are rigidly assembled with the housing 10.

Hereinafter, an explanation on the methods of packaging and distributing the product of the present invention, the operating states thereof, and the usage thereof will be given.

For the distribution of the product of the present invention, four parts, that is, the housing 10 assembled with the wheel gear 20, the wheel cup 30, and the joint gear 40 therein by means of the stop key 19, the tube 50 charged with the dentifrice material, the link 60, and the lid 70 are individually packaged, and then, they are assembled by a user before the use.

In order to use the product of the present invention, then, after the parts of the product are unpackaged, the sticker attached on the tube inlet 51a of the tube 50 is removed and the tube 50 is housed in the tube room 15 of the housing 10.

First, at the state where the tube inlet 51a is disposed correspondingly to the neck portion insertion hole 14b of the housing 10, the neck portion 51 is taken by means of tweezers, and the compressing ring 52b is pressed to push into the neck portion insertion hole 14b.

Consequently, the fixing ring 52a is tightly inserted into the ring groove 14c at the inside of the head portion 14 through the neck portion insertion hole 14b, such that the tube 50 is fitted to the neck portion insertion hole 14b, without any natural separation from the tube room 15 before the application of arbitrary forces by a user.

At this time, the tube 50 is placed into the tube room 15 at the state where the back plate 54a is spaced apart from the partition 16 of the housing 10.

After the tube 50 charged with the dentifrice material is mounted into the tube room 15, the link 60 is disposed into the link room 17 of the housing 10.

Referring to the method for mounting the link 60 into the link room 17, first, the link shaft 60a is disposed correspondingly at the partition groove 16a so as to fit the push panel 62 between the back plate 54a and the partition 16, and the ratchets 67a and 67b elastically formed on the both end portions of the rear side of the link 60 are disposed correspondingly to the backmost of the teeth 18, such that the link 60 is mounted into the link room 17 of the housing 10. The link pillar 63 is passed through the link guide 72, and the lid rim 71 is fitted correspondingly along the insertion groove 15a of the inner peripheries of the top sides of the vertical walls of the tube room 15 and the link room 17. Then, the pillar-like locking protrusions 17a formed at both corners of the opened side of the link room 17 are disposed correspondingly at the corner grooves 73a and 73b of the lid 70, and if the lid 70 is evenly pressed by the application of the external force on the top surface thereof, the lid rim 71 is fitted to the insertion groove 15a of the housing 10, thereby finishing the assembling process of the disposable dental prophylaxis apparatus according to the present invention.

If the product of the present invention is to be used for conducting dental operations, a hand motor connection reference groove 12b formed on the outer periphery of the thick tube 12 of the housing 10 is disposed correspondingly at a reference protrusion of a hand motor and is then pushed fittably thereto.

Consequently, the shaft end portion 41a of the joint gear 40 is fittably inserted into a connection hole of the hand motor, and at this state, if the locking mechanism of the hand motor is rotated in one direction, the housing 10 is fixed to the hand motor by means of a fixing device of the hand motor, thereby finishing the preparation before the use of the product of the present invention.

Therefore, if a switch is turned on at a state where the hand motor is taken by a dentist's hand, the hand motor is rotated to rotate the joint gear 40, and at the same time, the wheel gear 20 that is in perpendicular engagement with the joint gear 40 is accordingly rotated, thereby causing the wheel cup 30 coupled with the wheel gear 20 to be rotated together with the wheel gear 20.

Next, at the state where the hand motor is taken by the dentist's hand if the push button 64 is pressed in one direction by using his or her free finger, the link 60 is moved forwardly in the same direction as applied by pressing the push button 64.

At this time, while the link 60 is moved in one direction by the application of the pushing force of the push button 64, the shaft 60a is moved in one direction by the guide of the partition groove 16a, and the guides 65a and 65b formed at the bottom and top faces of the both rear sides of the shaft 60a are moved in one direction by the guide of the ceiling face of the lid 70 and the bottom face of the link room 17, without any up or down movement. Also, the pillar 63 is stably moved along the link guide 72 of the lid 70.

On the other hand, a pressure generated when the link 60 is pushed by a finger just generates one click sound caused when the push button 64 is pressed by the finger.

The pressure making the click sound of one time also causes the impact generated when the ratchets 67a and 67b formed on the both sides of the rear portion of the link 60 move one of the plurality of teeth 18, and when the ratchets 67a and 67b move one of the plurality of teeth 18, the push panel 62 pressurizes the back plate 54a of the tube 50 by the pressure corresponding to the moving distance of the link 60.

Thus, the tube 50 having the pressure applied from the link 60 generates the expanded pressure to cause the dentifrice material charged therein to flow through the tube inlet 51a, and the dentifrice material is moved toward the drain hole 21 of the wheel gear 20 through the drain hole 14a of the housing 10. Next, the dentifrice material is passed toward the friction space portion 33a of the wheel cup 30 through the drain hole 32 of the wheel cup 30, and it is supplied to the grinding wings 33 at the state of keeping rotated, such that the grinding wings 33 rub against the surface of the patient's tooth.

As described in the foregoing, the disposable dental prophylaxis apparatus according to the present invention has all parts made of synthetic resin giving no harms to a human body, and as it has the whole size having a length of about 65 mm, a height of about 16 mm, and a width of about 13.5 mm and the respective drain holes have a diameter of about 1.5 mm, it is relatively small and compact such that it can be made in great large quantities at relatively inexpensive costs. Further, it is designed to be available easily and conveniently and is also tested with a finished product sample, such that it is found that the present invention has remarkably apparent novelty and originality when compared with the conventional practices where no embodiments have been put into practical use in the related art. Thus, the present invention can eliminate many inconveniences that the hand motor should be turned on and off repeatedly whenever the dental operation is moved to one tooth to another tooth so as to supply the dentifrice material to the moved tooth.

Moreover, the product of the present invention can eliminate many inconveniences that whenever the dentifrice material is continuously compensated so as to perform the dental operations, the product should be put and drawn repeatedly into/from the patient's mouth.

The operation principles between the structures of the tube and the link are based upon the principles of syringes accustomed well by the dentist's hand in their use, such that the dentists can skillfully use the product of the present invention, without having any inconveniences.

That is to say, the dentist can push the link by his or her finger in such a manner where the push rod of the piston of a syringe is pushed, at the state where the product of the present invention is taken by his or her other fingers or hand, and in this case, he or she can recognize the movement of the ratchets along the teeth of the link room through the finger pushing the link, such that the dentifrice material can be supplied in a predetermined amount at any given time, in the same manner as to discharge the liquid from the syringe, which enables the dental operations to be kept performed.

In addition, the disposable dental prophylaxis apparatus according to the present invention has the head portion formed obliquely thereto in such a manner as to be inserted deeply into the patient's mouth, which enables the dental operations to be performed even to children patients having a substantially small mouth structure.

The invention has been described in al illustrative manner. It is to be understood that the terminology which has been used is intended to be in the nature of words of description rather than of limitation. Many modifications and variations of the invention are possible in light of the above teachings. Accordingly, the scope of the invention should not be construed as limited to this specific embodiment depicted and described, but rather as defined in the claims appended hereto.

I claim:

1. A disposable dental prophylaxis apparatus capable of discharging a predetermined amount of dentifrice material therefrom, comprising:

a housing having a hollow portion terminating in a head portion with a wheel room formed at said head portion in said housing and wherein a drain hole is formed to serve as a passageway between said wheel room and a tube room formed in said housing having wall surfaces and wherein said tube room is in front of a link room formed in said housing having inside wall surfaces with a plurality of teeth formed along said inside wall surfaces of said link room for arbitrarily adjusting the discharge of said dentifrice material in predetermined amounts and wherein an entrance is formed opened at a back side portion of said link room;

a tube mounted in said tube room and having a back plate;

a link having a link shaft and a push panel formed at a front end portion of said link shaft; and said link mounted in said link room in such a manner as for said push panel to be in close contact with said back plate of said tube to apply compressive force to said tube;

a partition formed between said link room and said tube room, and having a partition groove adapted for guiding said link;

a lid having a link guide formed so as to open a given distance in one direction thereof;

an insertion groove formed along a top portion of said wall surfaces of said tube room and said inside wall surfaces of said link room in such a manner as to be coupled with said lid therealong after said tube and said link are mounted in said tube room and said link room, respectively;

a joint gear with an outer peripheral surface and a wheel gear with a bottom face both rotatably mounted in said hollow portion of said housing; and a wheel cup having a lower portion, a middle portion, a wheel cup drain hole formed in said wheel cup to pass through said middle portion for receiving said dentifrice material therethrough, a top periphery with a ring-shaped close contact face formed along said top periphery, an inner periphery of said ring-shaped close contact face, an elastic close contact groove formed along said inner periphery of said ring-shaped close contact face, and wherein said ring-shaped close contact face and said elastic close contact groove are adapted for close contact with said head portion of said housing and with said bottom face of said wheel gear.

2. The disposable dental prophylaxis apparatus according to claim 1, wherein said head portion of said housing is formed obliquely and extends downwardly at a front edge portion thereof whereby it can be inserted deeply into the patient's mouth; and wherein said drain hole in said housing is formed curved along a middle portion of said head portion in such a manner as to communicate with said wheel room.

3. The disposable dental prophylaxis apparatus according to claim 1, wherein said tube has a tube inlet and said tube room comprises a needle formed protrudedly along an outer periphery of an inlet of a neck portion insertion hole in such a manner as to openably penetrate a sealed material on said tube inlet when said tube pushed into said tube room.

4. The disposable dental prophylaxis apparatus according to claim 1, wherein said hollow portion of said housing is adapted for mounting said joint gear and said wheel gear in the lengthwise direction thereof, said hollow portion having an area of circular cross section.

5. The disposable dental prophylaxis apparatus according to claim 1, wherein said hollow portion of said housing is adapted for mounting said joint gear and said wheel gear in the lengthwise direction thereof, said hollow portion having an area of ovular cross section.

6. A disposable dental prophylaxis apparatus capable of discharging a predetermined amount of dentifrice material therefrom, comprising:

a housing having a hollow portion terminating in a head portion with a wheel room formed at said head portion in said housing and wherein a drain hole is formed to serve as a passageway between said wheel room and a tube room formed in said housing having wall surfaces and wherein said tube room is in front of a link room formed in said housing having inside wall surfaces with a plurality of teeth formed along said inside wall surfaces of said link room for arbitrarily adjusting the discharge of said dentifrice material in predetermined amounts and wherein an entrance is formed open at a back side portion of said link room;

a tube mounted in said tube room and having a tube body, a front plate, and a back plate; and wherein said front and back plates are formed relatively thicker than said tube body;

a link having a link shaft, a push panel, a first ratchet, a second ratchet, and a push button; and wherein said first and second ratchets are elastically formed on both sides of a rear end portion of said link shaft in such a manner as to be moved in one direction along said plurality of teeth in said inside wall surfaces of said link room; and wherein said push button is formed extended from a vertical pillar formed on a top side of a center portion of said rear end portion of said link shaft, and said push button is mounted at a given inclination angle in such a manner as to easily be pushed by a finger; and wherein said push panel is formed at a front end portion of said link shaft; and wherein said link is mounted in said link room in such a manner as for said push panel to be in close contact with said back plate of said tube to apply compressive force to said tube;

a lid having a link guide formed so as to open a given distance in one direction thereof;

a joint gear with an outer peripheral surface and a wheel gear with a bottom face both rotatably mounted in said hollow portion of said housing; and a wheel cup having a lower portion, a middle portion, a wheel cup drain hole formed in said wheel cup to pass through said middle portion for receiving said dentifrice material therethrough, a top periphery with a ring-shaped close contact face formed along said top periphery, an inner periphery of said ring-shaped close contact face, an elastic close contact groove formed along said inner periphery of said ring-shaped close contact face, and wherein said ring-shaped close contact face and said elastic close contact groove are adapted for close contact with said head portion of said housing and with said bottom face of said wheel gear.

7. The disposable dental prophylaxis apparatus according to claim 6, wherein said head portion of said housing is formed obliquely and extends downwardly at a front edge portion thereof whereby it can be inserted deeply into the patient's mouth; and wherein said drain hole in said housing is formed curved along a middle portion of said head portion in such a manner as to communicate with said wheel room.

8. The disposable dental prophylaxis apparatus according to claim 6, wherein said tube has a tube inlet and said tube room comprises a needle formed protrudedly along an outer periphery of an inlet of a neck portion insertion hole in such a manner as to openably penetrate a sealed material on said tube inlet when said tube pushed into said tube room.

9. The disposable dental prophylaxis apparatus according to claim 6, wherein said hollow portion of said housing is adapted for mounting said joint gear and said wheel gear in the lengthwise direction thereof, said hollow portion having an area of circular cross section.

10. The disposable dental prophylaxis apparatus according to claim 6, wherein said hollow portion of said housing is adapted for mounting said joint gear and said wheel gear in the lengthwise direction thereof, said hollow portion having an area of ovular cross section.

\* \* \* \* \*